Figure 1:
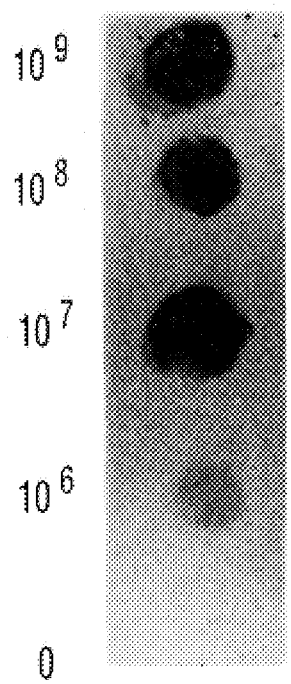

United States Patent [19]
Zawistowski

[11] Patent Number: 5,807,694
[45] Date of Patent: Sep. 15, 1998

[54] **DETECTION OF *SALMONELLA ENTERITIDIS* AND OTHER PATHOGENIC MICROORGANISMS AND MONOCLONAL ANTIBODY USEFUL THEREFOR**

[75] Inventor: Jerzy Zawistowski, Winnipeg, Canada

[73] Assignee: Economic Innovation and Technology Council, University of Manitoba, Winnipeg, Canada

[21] Appl. No.: 524,506

[22] Filed: Sep. 7, 1995

[51] Int. Cl.$^6$ .................. G01N 33/569; G01N 33/53; C12N 1/20
[52] U.S. Cl. ............. 435/7.35; 435/7.1; 435/7.2; 435/7.32; 435/174; 435/243; 435/252.8
[58] Field of Search ................. 424/137.1, 141.1, 424/150.1, 157.1, 178.1; 435/7.35, 7.2, 7.1, 7.32, 174, 243, 252.8

[56] References Cited

U.S. PATENT DOCUMENTS

| | | |
|---|---|---|
| 3,932,672 | 1/1976 | Pour-El . |
| 4,364,966 | 12/1982 | Chang . |
| 4,683,196 | 7/1987 | McLaughlin . |
| 4,834,975 | 5/1989 | Siadak et al. . |
| 4,870,158 | 9/1989 | Karol et al. . |
| 4,906,567 | 3/1990 | Connelly . |
| 4,918,163 | 4/1990 | Young . |
| 5,169,757 | 12/1992 | Yamazaki et al. . |
| 5,179,018 | 1/1993 | Bogard, Jr. et al. . |

FOREIGN PATENT DOCUMENTS

| | | |
|---|---|---|
| 2078162 | 3/1994 | Canada . |
| WO 8601805 | 3/1986 | WIPO . |

OTHER PUBLICATIONS

Lee et al; Food and Agricultural Immunology (1989)1, 89–99.

Thorns et al; J. of Clinical Microbiology, Nov. 1990 Vo.28, No. 11 pp. 2409–2414,.

Brigmon et al; J. of Immunological Methods, 152(1992) pp. 135–142.

Lu et al.; FEMS Microbiology Letters 80 (1991) 135–140.

Blais et al; Int.J. of Food Microbiology, 20 (1993) 149–158.

Cerqueira–Carpos Appl & Env. Microb. 52:124–127, 1986.

Masi & Zawistowski, Food & Agicrul. Immunol 7:351–363, 1995.

Elsarnagawy, Archives de L'Inst. Pastuer 53:282–290, 1978–1979.

Promega Protocols and Applications Guide 1991 pp. 221–226 and 262–269.

*Primary Examiner*—Toni R. Scheiner
*Assistant Examiner*—Nancy A. Johnson

[57] ABSTRACT

A method of testing for the presence of a pathogenic microorganism, notably *Salmonella enteritidis*, in a foodstuff, e.g. the contents of an egg, or other materials. In a particularly preferred form for testing eggs, the method involves homogenizing a sample of the egg, incubating the egg contents to enrich any pathogen present, adding a detergent to release antigens from pathogen cell surfaces, heating the egg contents to gell them and then carrying out a dot-blot assay of the gelled egg material to detect the presence of the antigens. The method is particularly applicable to $D_1$ serovars of *Salmonella enteritidis*. The antibody used in the method is preferably a novel $IgG_{2\alpha}$ type immunoglobulin having a lambda light chain, designated as MAb 2F11, which can also be used for other methods of testing for *Salmonella enteritidis* and other $D_1$ serovars, and for passive protection of poultry against infections by such pathogens.

17 Claims, 6 Drawing Sheets ns of *Salmonella enteritidis* (Serogroup D₁; 1,9,12:g,m:-,) infec-

DETECTION OF SALMONELLA ENTERITIDIS AND OTHER PATHOGENIC MICROORGANISMS AND MONOCLONAL ANTIBODY USEFUL THEREFOR

BACKGROUND OF THE INVENTION

I. Field of the Invention

This invention relates to methods of detection of pathogenic microorganisms, such as bacteria, in foodstuffs or other materials. More particularly, although not exclusively, the invention relates to the detection of the common phage types of *Salmonella enteritidis* and other $D_1$ serovars in eggs and poultry meats, and to monoclonal antibodies that may be used for detecting such organisms.

II. Description of the Prior Art

Illness and poisonings due to pathogenic organisms in foodstuffs seem to be on the increase in the developed nations of the world. In particular, the implications of *Salmonella enteritidis* (Serogroup $D_1$; 1,9,12:g,m:-,) infections in humans have become an important international health issue. In Great Britain, reported infections have risen by 250% from 12,000 cases per year in 1982 to 31,000 cases per year in 1992 (Roberts and Sockett, Int. J. Food Microbiol. (1994) 21:117). This increase seems to parallel what is happening in the United States and other countries. The number of *Salmonella enteritidis* outbreaks in the United States increased from 26 in 1985 to 77 in 1989, involving 44 deaths (Mason, Int. J. Food Microbiol. (1994)21:155). In Canada, although the increase in prevalence of this pathogen in people has not been as dramatic as in Europe and the United States, infections due to *Salmonella enteritidis* increased to 12.5% in 1991, ranking it the second most commonly isolated serovar after *S. typhimurium* (Lior and Khakhria, Safety Watch (1992)27:3).

The cost of individual outbreaks of salmonellosis has been estimated in many countries. One outbreak of *Salmonella enteritidis* in the U.S. in 1985, for example, was estimated to have cost $62 million. The national costs of the illness in the Great Britain for 1992 was about £321 million. In one year alone (1989), the British government spent about £1 million compensating farmers for losses associated with *Salmonella enteritidis* infections in poultry (Roberts and Sockett, Int. J. Food Microbiol (1994)21:117).

Epidemiological investigations conducted worldwide have determined that fresh shell eggs and egg products are important vehicles of infection by *Salmonella enteritidis*. Contamination of eggs with this pathogen may occur via horizontal or vertical transmission of the bacteria. Horizontal contamination is caused by penetration of the bacteria through the shell when the egg is soiled with contaminated faeces (Catalano and Knabel, J. Food Prot. (1994)57:592), while vertical transmission occurs by transovarian infection caused by contamination in the bird ovary during egg formation (Lock et al, FEMS Microbiol. Let. (1992)100:71). Vertical contamination may also occur in the oviduct before the egg is covered by the shell. Consequently, the spread of vertical infection may quickly proliferate within flocks when birds are hatched from infected embryonated eggs. Vertical transmission is the significant route of contamination of eggs with *Salmonella enteritidis*. In Britain *Salmonella enteritidis*, phage type (PT) 4, has been recognized as a predominant strain associated with vertical infection, while PT 8 and 13 seem to be the major strains in the U.S. It is worthwhile to note that *Salmonella enteritidis* in eggs originating from vertical infection is always present in the pure culture, although organisms were isolated in small numbers (about 1 cell/ml) from naturally contaminated eggs (Humphrey, Int. J. Food Microbiol. (1994)21:31).

Infection by *Salmonella enteritidis* threatens the safety of human consumers and the economic soundness of the egg and poultry industry, as well as the food industry in general. The severe outbreak of this organism in 1988 alone in Britain resulted in a permanent 20% loss in volume of the egg market (U.S. Department of Agriculture, *Salmonella enteritidis* Task Force (1990)). Its control and elimination requires early detection in raw shell eggs. Traditional methods for detection of *Salmonella enteritidis* in eggs are scarce and require up to one week in order to culture and identify bacterial isolates. These methods are also labour-intensive, involve isolation of the organism using pre-enrichment as well as selective enrichment procedures and serological confirmation tests (Van der Zee, Int. J. Food Microbiol. (1994)21:41). More rapid methodology available for serological detection of *Salmonella enteritidis* is represented by two basic enzymatic-linked immunoassay (ELISA) procedures, the sandwich and indirect ELISA. Both employ antisera as well as monoclonal antibodies produced against flagella, lipopolysaccharides (LPS) and fimbriae SEF14 (Van Zijderveld et al., J. Clin. Microbiol. (1992) 30:2560). In contrast to conventional methods, these tests can detect *Salmonella enteritidis* in two days. However, they are not free of drawbacks. The tests involve time-consuming enrichment incubations, exhibit varying degrees of cross-reactions, particularly between serogroup B (*S. typhimurium*) and D lipopolysaccharides and both systems have been known to produce false positive reactions.

Most current information pertaining to epidemiology, virulency, prevention and detection of *Salmonella enteritidis* has been reviewed in the special issue of the International Journal of Food Microbiology (1994) 21.

SUMMARY OF THE INVENTION

An object of the invention, in one of its preferred forms, is to provide a method of detecting pathogenic microorganisms, particularly *Salmonella enteritidis* and other $D_1$ serovars, in foodstuffs, particularly eggs and poultry meats, involving a rapid and simple procedure.

Another object of the invention, in one of its preferred forms, is to provide a method capable of reliably detecting low concentrations of cells of pathogenic microorganisms, particularly *Salmonella enteritidis* and other $D_1$ serovars.

Another object of the invention, in one of its preferred forms, is to provide a method of testing for pathogenic microorganisms, particularly *Salmonella enteritidis* and other $D_1$ serovars, that is quite specific to the target organism.

Another object of the invention, is to provide a monoclonal antibody that binds with good exclusivity to an antigen of *Salmonella enteritidis* or to live and heat-treated cells, and that consequently can be used for detecting this organism in foodstuffs and other materials.

Yet another object of the invention, at least in a preferred form, is to provide a novel method of producing a monoclonal antibody from a hybridoma cell line.

According to a first aspect of the invention, there is provided a method of testing for the presence of a pathogenic microorganism in an egg, comprising: aseptically homogenizing a sample of the egg to form a uniform egg matrix; incubating the egg matrix for a period of time and at a temperature to cause propagation of the microorganism present in the matrix; adding a detergent to the incubated matrix to separate antigen molecules from surfaces of cells of the microorganism and to distribute the antigen molecules throughout the egg matrix; heating said egg matrix to cause gellation of said matrix; contacting the gelled egg matrix with an absorbent inert support to cause transfer of the antigen molecules present in said gelled matrix to said support; contacting said support with a detector antibody for said antigen to form antigen-antibody complexes with antigen present on said support; and detecting antigen-antibody complexes present on said support.

A particularly preferred form of the invention provides a method of testing for the presence of *Salmonella enteritidis*, or other $D_1$ serovar of Salmonella, in contents of an egg, comprising: aseptically accessing said contents within said egg; incubating the contents for a period of time and at a temperature to cause propagation of any *Salmonella enteritidis* or said other $D_1$ Salmonella serovar, present in the contents; adding a detergent to the incubated contents to release antigen from cells of said *Salmonella enteritidis* or said other $D_1$ Salmonella serovar; heating the contents to a temperature that causes gelling to form gelled egg contents; contacting said gelled egg contents with an absorbent inert support to cause transfer of said antigen, if present in said gelled egg contents, to said support by diffusion; contacting said support with an antibody directed against *Salmonella enteritidis* lipopolysaccharide O-9 to form antigen-antibody combinations with any *Salmonella enteritidis* antigen present on said support; and detecting any antigen-antibody combinations on said support.

A method of testing from the presence of a pathogenic microorganism in a foodstuff, other than egg, or other material, comprising: aseptically blending pre-enriched sample of the foodstuff or other material with liquid egg to form a matrix; incubating the matrix for a period of time and at a temperature to cause propagation of the microorganism present in the matrix; adding a detergent to the incubated matrix to separate antigen molecules from surfaces of cells of the microorganism and to distribute the antigen molecules throughout the egg matrix; heating said matrix to cause gellation of said matrix; contacting the gelled matrix with an absorbent inert support to cause transfer of the antigen molecules present in said gelled matrix to said support; contacting said support with a detector antibody for said antigen to form antigen-antibody complexes with antigen present on said support; and detecting antigen-antibody complexes present on said support.

The invention also provides a method of testing for *Salmonella enteritidis* or other $D_1$ serovars of Salmonella in a sample of a material, comprising: incubating said sample in a culture medium suitable for growth and propagation of said *Salmonella enteritidis*; adding a detergent to said culture medium; and testing for the presences of said *Salmonella enteritidis* in said culture medium by an enzymatic-linked immunosorbent assay using bound MAb 2F11 antibody.

Other aspects of the invention relate to novel monoclonal antibodies useful in the above methods and their use in other tests and systems. The invention also relates to the production of such antibodies.

The invention makes it possible to detect *Salmonella enteritidis* and other pathogens reliably in eggs, poultry meats and other materials.

Reference is made in this disclosure to dot-blot assays or tests. It should be noted that this term is intended to include so-called "strip-blot" assays and tests and, in general, any assay or test that involves the diffusion or other transfer of an antigen from a solid, semi-solid or gel-like or liquid sample material to a solid support.

BRIEF DESCRIPTION OF THE DRAWINGS

FIG. 1 shows dot-blot immunoassays of egg samples containing various levels of *Salmonella enteritidis* PT 4;

FIG. 2 shows the partial structures of B, $D_1$ and $D_2$-serogroup Salmonella O-antigens (adapted from Griffiths & Davies, Carbohydrate Polymers (1991) 14:241; and Lindberg & Le Minor, Meth. Microbiol. (1984) 15:1; the disclosures of which are incorporated herein by reference);

FIG. 3A shows an immunoelectron transmission microscopy image at 20,000× magnification of live *Salmonella enteritidis* PT 4 cells live, the Figure also shows the labelling of *S. enteritidis* by the anti-LPS-O9 MAb 2F11 antibody of one form of the invention conjugated with colloidal gold particles; this Figure shows the labelling of *S. enteritidis* by the anti-LPS-O9 Mab 2F 11 antibody of one form of the invention conjugated with colloidal gold particles;

FIG. 3B is an immunoelectron transmission microscopy image at 20,000× magnification of *Salmonella enteritidis* PT 4 cells heat-treated at 80° C. for 20 minutes, this figure also shows the labelling of *S. enteritidis* by the anti-LPS-O9-Mab 2F11 antibody of one form of the invention conjugated with colloidal gold particles;

FIG. 3C is is an immunoelectron transmission microscopy image at 20,000× magnification of *Salmonella enteritidis* PT 4 cells heat-treated at 100° C. for 10 minutes in the presence of 15% sodium cholate; this Fig. shows that heat-treated bacterial cells in the presence of sodium cholate are free of lipopolysaccharides and thus the released molecules are distributed within a solid food matrix and thus available for dot-blot assay.

FIG. 4 shows an ELISA standard curve (using poly-L-lysine pre-coated microplates) of *Salmonella enteritidis* in PBS buffer, each point representing the mean of three replicates;

FIG. 5 shows the results of an SDS-polyacrylamide gel electrophoresis of lipopolysaccharides extracted from different bacteria and developed by silver staining; Lanes: (1) *E. coli* (Sigma), (2) *S. typhimurium* (Sigma), (3) *S. enteritidis* (Sigma), (4) *S. enteritidis* PT 1, (5) *S. enteritidis* PT 4, (6) *S. enteritidis* PT 8, (7) *S. enteritidis* PT 13, (8) *S. enteritidis* PT 13a, (9) *S. gallinarum*, (10) *S. pullorum*, (11) *S. berta*, (12) *S. maarseen*; and FIG. 6 shows the results of an immunoblot of SDS-PAGE of lipopolysaccharides extracted from different bacteria (corresponding to gel of FIG. 5) and probed with MAb 2F11; Lanes: (1) *E. coli* (Sigma), (2) *S. typhimurium* (Sigma), (3) *S. enteritidis* (Sigma), (4) *S. enteritidis* PT 1, (5) *S. enteritidis* PT 4, (6) *S. enteritidis* PT 8, (7) *S. enteritidis* PT 13, (8) *S. enteritidis* PT 13a, (9) *S. gallinarum*, (10) *S. pullorum*, (11) *S. berta*, (12) *S. maarseen.*

DETAILED DESCRIPTION OF THE INVENTION AND THE PREFERRED EMBODIMENTS

Stated in general terms, a first aspect of the present invention relates to method of testing for pathogenic microorganisms, particularly bacteria, in foodstuffs or other materials. For clarity, however, the invention will be described as it relates to testing for *S. enteritidis* in eggs, and then the extension of the method to other pathogens and materials will be explained.

I. METHOD OF DETECTION FOR SALMONELLA ENTERITIDIS IN EGGS

The method of the invention, when used for testing for *S. enteritidis* specifically in eggs (normally commercial chicken's eggs), utilizes a two-step procedure comprising an enrichment step and a dot-blot assay. This aspect of the invention is based in part on the discovery that a small concentration of cells of Salmonella enteritidis can be enriched to a detectable number (e.g. from 1–5 cell/ml up to $10^6$–$10^7$ cell/ml) directly in the homogenized whole egg without the need to isolate the organism and without the need to use large volumes of enrichment broth, thus overcoming a disadvantage of conventional known processes.

Another basis of this aspect of the invention is the discovery that the lipopolysaccharide antigen of *Salmonella enteritidis*, once released from the bacterial cells, can be uniformly distributed in an egg gel network formed by heating, which permits easy blotting of the antigen onto a solid support, such as a porous membrane.

In a preferred form of the method, a whole shell egg suspected of being contaminated even with a low number of *Salmonella enteritidis* cells is cracked open aseptically and then the contents are blended and incubated at a suitable temperature, e.g., 37° C., overnight or for an equivalent period of time of about 6 to 20 hours. The liquid egg contents are then mixed with a detergent, e.g., a 15% sodium cholate solution in phosphate buffered saline (PBS, pH 7.2). Other suitable detergents include sodium deoxycholate, cholic acid, sodium dodecylsulphate, TWEEN (trademark) 20, TWEEN 80, and TRITON (trademark) 100. Of these, sodium cholate followed by cholic acid, sodium deoxycholate and TRITON 100 are the most efficient detergents. There may also be other efficient derivatives of cholic acid, e.g. different metal salts. The detergents should preferably be added after the incubation and propagation of the *S. enteritides* cells since addition during the incubation phase could disturb the growth of the bacteria and thus result in insufficient production and release of detectable lipopolysaccharides.

The mixture containing the detergent is immediately heated at about 100° C. for 10 minutes to gel the egg contents and then cooled to room temperature. Heating the egg contents in the presence of the detergent yields lipopolysaccharides free from any *Salmonella enteritidis* cells present in the mixture, and these lipopolysaccharides are dispersed and trapped in the gelled egg network formed upon heating.

The solidified egg mixture is next cut into discs of a convenient size (preferably about 1 cm in diameter and 2–4 mm thick) and the discs are placed on a pre-wet 0.45 μm nitrocellulose membrane strip, forming a solid support, and left in contact with the strip for at least about 5 minutes at room temperature. This produces a blot transfer of the lipopolysaccharide antigen of *Salmonella enteritidis* from the solidified egg to the membrane via diffusional forces.

An alternative transfer of antigen to the membrane can be brought about by placing a strip of a solid support, such as a pre-wet nitrocellulose membrane (1×5 cm), on the solidified egg mixture for at least about five minutes at room temperature. The blot assay can employ various solid supports in the form of membranes made from a variety of materials, such as nitrocellulose, ester nitrocellulose, cellulose acetate, polyvinylidene difluoride (PVDF), nylon (neutral, and positively charged), diazobenzyloxymethyl, diazophenylthioether, and polyester such as polyethyleneterephthalate (DACRON; a trade mark of DuPont), etc.

The resulting blot on the solid support is then contacted with an antibody, preferably a biotinylated mouse monoclonal antibody, specific to lipopolysaccharide O-9 (LPS O-9) antigen, and the presence of the antigen is detected by any convenient method of detecting formed antigen-antibody complexes, e.g., by incubating the complex with streptavidin-alkaline phosphatase conjugate and 5-bromo-4-chloro-3-indylphosphate ρ-toluidine salt/nitroblue tetrazolium chloride substrate solution (BCIP/NBT). The formation of a black colour is considered to be an indication of the presence of *Salmonella enteritidis.*

Alternatively, the transferred blot may be contacted with a mouse monoclonal antibody specific to LPS O-9, and any antigen-antibody complex thus formed may be detected by incubation with a biotinylated goat (rabbit or other host animal) anti-mouse antibody, followed by streptavidin-alkaline phosphatase conjugate and substrate solution. The antigen-antibody complex can further be detected by incubation with an anti-mouse antibody conjugated with streptavidin followed by biotylinated alkaline phosphatase and substrate solution.

Another approach that may be used to detect the transferred antigen, if present, is by contacting the blot with a biotinylated mouse monoclonal antibody specific to LPS O-9, followed by incubation with free streptavidin and biotinylated alkaline phosphatase and substrate solution. Moreover, avidin can be used instead of streptavidin, while alkaline phosphatase can be replaced by any other suitable enzyme, such as peroxidase or glucose oxidase followed by respective substrate solution.

The detection limit of the dot-blot procedure is about $10^6$ cells/ml. Combined with the prior incubation step, in its optimum form, the assay requires less than 24 hours for the detection of as few as one cell/25 g of egg contents.

In contrast to other methods pertaining to the detection of bacterial lipopolysaccharides, this procedure does not require the extraction of the lipopolysaccharides themselves from the foodstuff. It has also been found that the blotting transfer is rapid and can be efficiently used to capture the lipopolysaccharide antigen onto a membrane, and the blotted membrane can then be subsequently used for reaction with, and detection by, a *Salmonella enteritidis*-specific antibody.

II. TESTING FOR PATHOGENS OTHER THAN *S. ENTERITIDIS* IN EGGS

When testing for pathogenic microorganisms other than *S. enteritidis*, it is necessary to adapt the incubation conditions (if necessary) from those illustrated above to encourage the propagation of the particular target pathogen and to use an antibody specific to antigens separated from cells of the target organism. Such modifications are believed to be within the expected skill of a person knowledgeable in this art.

Antibodies suitable for the method of the invention must have specificity and high avidity for the target pathogen as well as no undue reactions or incompatibility with components of the egg sample to be tested. While polyclonal antibodies (antisera) may be employed, monoclonal antibodies are preferred.

When the procedure is used for detecting strains of *S. enteritidis* and other $D_1$-serovars, a novel monoclonal antibody (MAb) designated MAb 2F11 is ideally employed for this purpose in the assay, this antibody being described in more detail below.

III. TESTING MATERIALS OTHER THAN EGGS

When testing for *S. enteritidis* and other $D_1$ serovars in foodstuffs other than eggs, e.g. poultry meats, or other materials (e.g blood, urine, etc.), the sample is blended with lactose broth or other suitable broth and then incubated at a warm temperature, e.g. about 37° C., for up to six hours. After incubation, a small portion (e.g. 1 ml) of enrichment broth is transferred to an amount, e.g. about 25 g, of homogenized liquid egg and mixed thoroughly. The mixture is then incubated for an additional 18 hours at about 37° C. The mixture is mixed with a detergent and converted into a form suitable for dot-blot assay in the manner indicated above. The solidified egg mixture containing the sample is then used for blotting, as described above.

Alternatively, the food (or other) sample may be subjected to an enrichment procedure as disclosed in the Bacteriological Analytical Manual (US FDA. 1984, Chap. VII In "Bacteriological Analytical Manual," 6th ed. p.1, Food and Drug Admin., Washington, D.C.) and the AOAC (AOAC.1995, Chap. 17, Subchap. 9 In "Official Methods of Analysis," p.55, Assn. Off. Anal. Chem., Arlington, Va.), the disclosures of which are incorporated herein by reference. The sample may also be enriched as described in Example 5 below. After enrichment, the broth is mixed with detergent and boiled for 10 minutes and cooled to room temperature. Then, a small amount (e.g. 100 $\mu$l) of the broth is spotted onto a nitrocellulose membrane strip and left in contact until dry in order to transfer the LPS antigen of S. enteritidis from the enrichment broth to the membrane. To detect S. enteritidis in the sample, the resulting blot is developed using MAb 2F11 as described above.

IV. MAb 2F11

Figure 2:
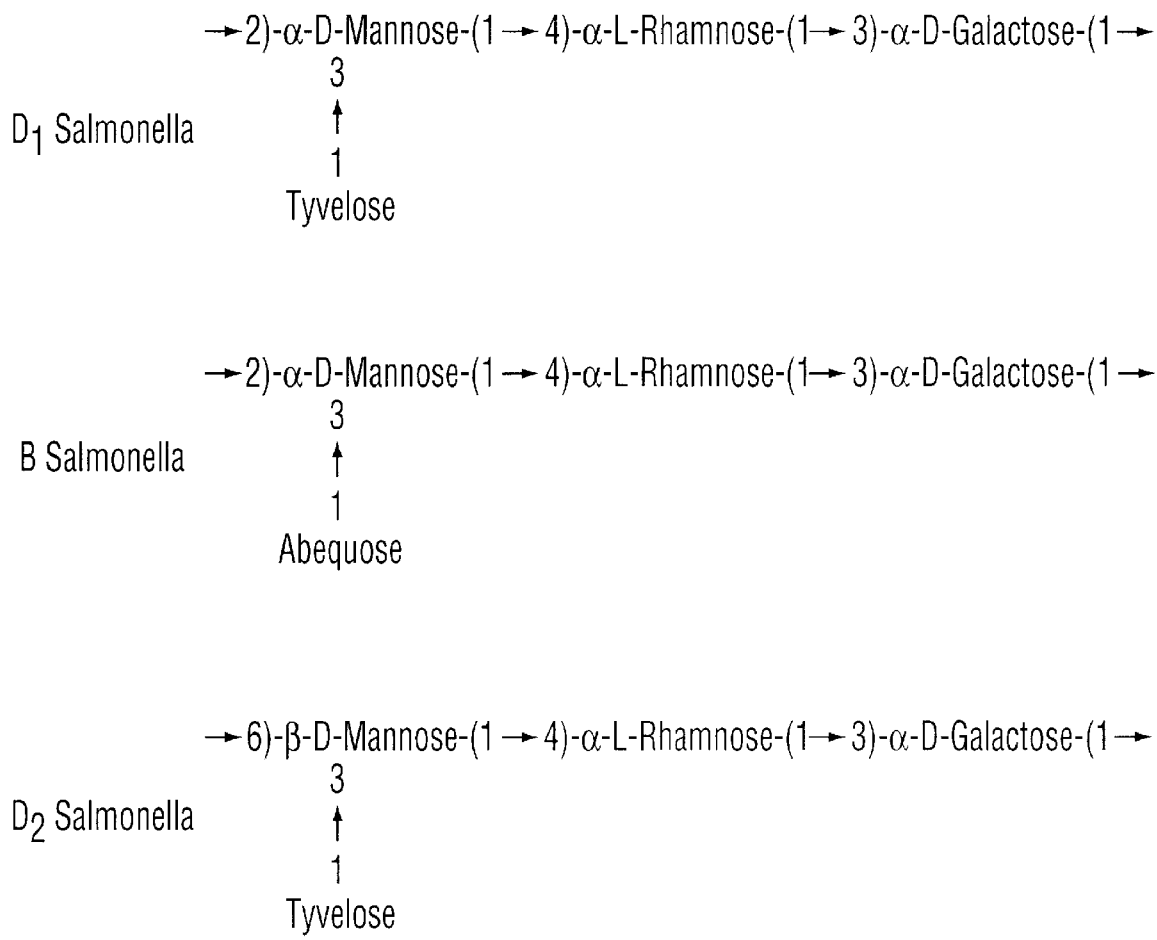

The novel monoclonal antibody MAb 2F11 binds specifically to the lipopolysaccharide O-9 antigen of the $D_1$-serogroup of Salmonella which is composed of a tetrasaccharide unit of mannose, rhamnose, galactose and tyvelose (see FIG. 2). This antibody is noteworthy in that it is able to react with live and heat-treated bacteria as well as with detached antigenic fragments. The MAb has high avidity towards various phage types of S. enteritidis, good recognition of live bacteria, high affinity to S. enteritidis, and good reactivity with S. enteritidis molecular markers (lipopolysaccharides) on membrane (in situ). It should also be noted that the MAb 2F11 can be used to detect other $D_1$-serovars than S. enteritidis, e.g. Salmonella berta, Salmonella gallinarum, Salmonella pulorum, etc. All $D_1$-serovars are predominantly avian (domestic fowl) pathogens and they are known to infect eggs.

Figure 3A:
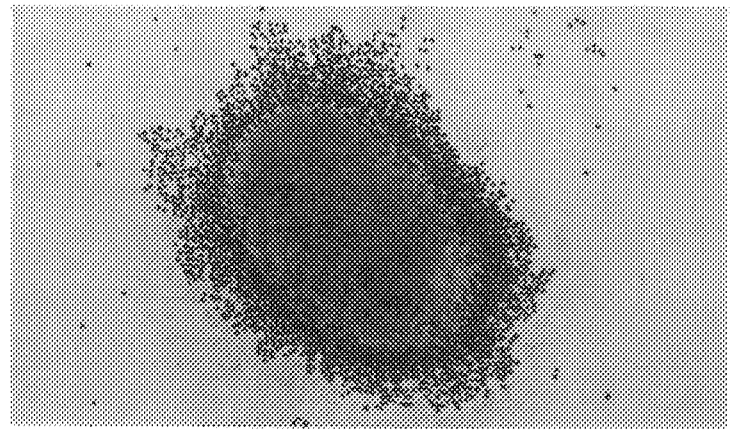
Figure 3B:
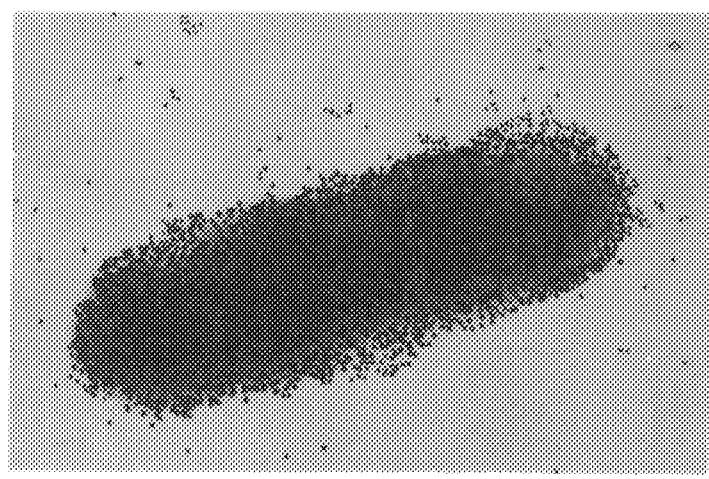
Figure 3C:
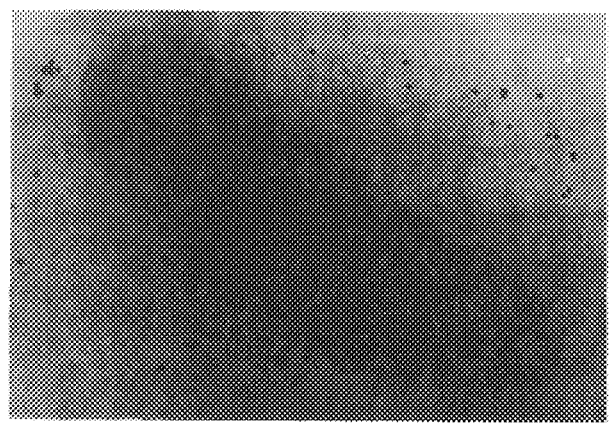

Although similar specificity has been reported for a monoclonal antibody developed by Lu et al (FEMS Microbiol. Let. (1991) 80:135), the novel MAb 2F11 is different in several respects. This monoclonal antibody is of the $IgG_{2a}$type immunoglobulin with a lambda light chain. The MAb 2F11 reacts with live bacteria (FIG. 3A), heat attenuated (e.g. at 80° C. for 20 minutes) bacteria (FIG. 3B) as well as with free lipopolysaccharides of Salmonella enteritidis.

The MAb 2F11 is highly reactive to all tested lipopolysaccharides of Salmonella enteritidis strains exhibiting equal avidity regardless of the phage type. This property makes MAb 2F11 a suitable probe for the detection of various phage types of Salmonella enteritidis with equal sensitivity in the assay format described in sections I and II above. Furthermore, the antibody is not reactive with compounds present in an egg matrix, and generally in other foodstuffs, which allows for a clear discrimination between positive and negative controls.

Table 1 below shows the specificity of MAb 2F11 as determined for a panel of heat-attenuated (80° C., 20 minutes) bacteria using a standard enzyme-linked immunoassay (ELISA) procedure.

TABLE 1

Specificity of MAb 2F11 to Salmonella enteritidis

| Serogroup | Bacteria | Antigenic Formula | Absorbance (405 nm) |
|---|---|---|---|
| $D_1$ | S. enteritidis PT 1[a] | 9,12:g,m:- | 1.925 |
| | S. enteritidis PT 4[a] | 9,12:g,m:- | 1.199 |
| | S. enteritidis PT 8[a] | 9,12:g,m:- | 1.048 |
| | S. enteritidis PT 13[a] | 9,12:g,m:- | 1.222 |
| | S. enteritidis PT 13a[a] | 9,12:g,m:- | 1.449 |
| | S. berta[b] | 9,12:f,g,t:- | 1.105 |
| | S gallinarum[c] | 9,12:-:- | 0.949 |
| | S. pullorum[b] | 9,12:-:- | 0.268 |
| $D_2$ | S. maarseen[b] | 9,46:$z_4$;$z_{24}$;$z_{39}$;$z_{42}$ | 0.017 |
| B | S. typhimurium[b] | 4,5,12:i:1,2 | 0.052 |
| | S stanley[c] | 4,5,12:d:1,2 | 0.021 |
| | S. brandenburg[d] | 4,12:1,v:e,n,$z_{15}$ | 0.017 |
| | S. agona[d] | 4,12:f,g,s:- | 0.020 |
| | S. schottmuelleri[c] | 4,5,12:b:1,2 | 0.020 |
| | S. albert[d] | 4,12:$z_{10}$:e,n,x | 0.031 |
| | S. kingston[d] | 4,12,27:g,s,t:- | 0.0311 |
| $C_1$ | S. thompson[c] | 6,7:k:1,5 | 0.016 |
| | S. cholerasuis[d] | 6,7:k:1,5 | 0.030 |
| | S. mbandaka[d] | 6,7:$z_{10}$:e,n,$z_{15}$ | 0.058 |
| $C_2$ | S. hadar[d] | 6,8:$z_{10}$:e,n,x | 0.033 |
| | S. muenchen[d] | 6,8:d:1,2 | 0.018 |
| $E_1$ | S. anatum[d] | 3,10:e,h:1,6 | 0.036 |
| $E_3$ | S. thomasville[d] | 15,34:y:1,5 | 0.043 |
| $E_4$ | S. senftenberg[e] | 3,9:g,s,t:- | 0.045 |
| F | S. rubislaw[d] | 11:r,:e,n,x | 0.029 |
| $G_2$ | S. havana[d] | 13,23:f,g(s):- | 0.035 |
| Atypical | S. arizona[c] | ND[e] | 0.034 |
| | B. coli[b] | ND | 0.054 |
| | E. coli[b] | ND | 0.044 |
| | Yersinia enterocolitica[d] | ND | 0.027 |
| | Citrobacter freundii[b] | ND | 0.045 |
| | Enterobacter cloacae[d] | ND | 0.046 |
| | Shigela flexneri[d] | ND | 0.031 |
| | Mycobacterium fortuitum[d] | ND | 0.059 |
| | Pseudomonas flourescens[d] | ND | 0.052 |
| | Aeromonas hydrophila[d] | ND | 0.048 |

[a]Laboratory Centre for Disease Control, Ottawa, Canada.
[b]American Type Culture Collection, Rockville, MD, USA.
[c]University of Manitoba Microbiology Department, Winnipeg, Canada.
[d]Economic Innovation Technical Centre; Winnipeg, Canada.
[e]ND- not determined.

The antibodies prominently reacted with all tested phage types of S. enteritidis (PT 1, 4, 8, 13, 13a), exhibiting the highest avidity towards PT 1. The MAb 2F11 reacts also with other $D_1$-serovars, displaying different degrees of binding. It appeared also that the monoclonal antibody shows no reactivity towards antigenetically similar S. maarseen of the $D_2$-serogroup as well as towards eight other tested Salmonella serogroups: B, $C_1$, $C_2$, $D_2$, $E_1$, $E_3$, $E_4$, F, $G_2$ and an atypical S. arizonae strain. In addition, a number of Enterobacteriaceae (E. coli, Y. enterocolitica, C. freundii, E. cloacae, S. flexneri) and other bacteria (M. fortuitum, P. fluorescens and A. hydrophila) do not bind to MAb 2F11.

Significantly, MAb 2F11 reacts with live S. enteritidis cells, giving similar absorbance values for all tested phage types as assessed by ELISA. Somewhat lower absorbance values are observed for determination of other $D_1$-serovars such as S. gallinarum, berta and pullorum and negative results are obtained for other bacteria, as shown in Table 2 below.

TABLE 2

Binding of MAb 2F11 to live Salmonella as assessed by ELISA

| Bacteria | Absorbance |
| --- | --- |
| S. enteritidis PT 1 | 0.916 |
| S. enteritidis PT 4 | 0.980 |
| S. enteritidis PT 8 | 1.092 |
| S. enteritidis PT 13 | 0.919 |
| S. enteritidis PT 13a | 0.989 |
| S. gallinarum | 0.831 |
| S. berta | 0.809 |
| S. pullorum | 0.313 |
| S. maarseen | 0.069 |
| S. typhimurium | 0.054 |
| E. coli | 0.058 |

Figure 4:
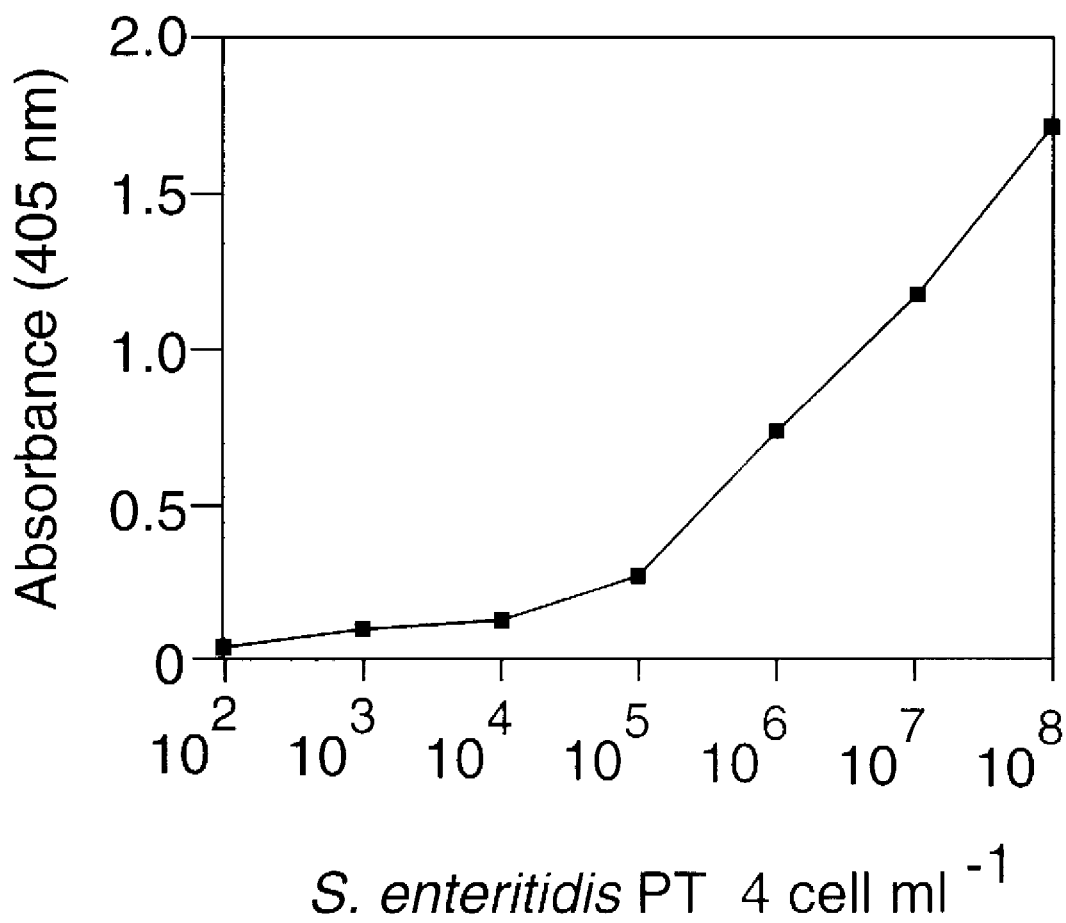

It can therefore be stated that Mab 2F11 is reactive with heat-attenuated as well as live S. enteritidis cells. In addition, this antibody exhibits high and equal avidity to lipopolysaccharides isolated from S. enteritidis regardless of phage types. The MAb 2F11 proves to be specific to lipopolysaccharides O-9 present in $D_1$-serogroup Salmonella. Immunoblotting and ELISA results have demonstrated that the epitope recognized by this antibody is partially composed of tyvelose and mannose and it was also determined by the nature of glycosidic bonds between monosaccharides in the polysaccharide backbone region. Employing poly-L-lysine pre-coated microplates, this antibody exhibits a detection limit of $10^4$ S. enteritidis cells/ml of buffer as assessed by ELISA (FIG. 4).

V. OTHER USES OF MAb 2F11

It appears that lipopolysaccharide O-9 antigenic sites are easy accessible by MAb 2F11 without the need for further heat or chemical treatment in order to expose the epitopes. These properties make the MAb 2F11 suitable for use in the isolation of live S. enteritidis cells from food, clinical and environmental samples in a single immunocapture step in ELISA. The immunocapture step, which employs antibodies immobilized on latex or magnetic beads, plastic tubes or dipsticks, significantly reduces the time needed for the detection of bacteria by elimination of a selective enrichment procedure.

It is of note that the majority of the protocols for the production of monoclonal antibodies against bacteria describe the use of bacterial cells attenuated chemically or by heating at 100° C. for mouse immunization. The inventor of the present invention has found, as a result of immunoelectron microscopy of *S. enteritidis*, that boiling bacterial cells efficiently removes cell-bound lipopolysaccharide molecules. In contrast, when *S. enteritidis* is less severely heated at 80° C. for 20 minutes (conditions used in the immunization protocol referred to below), some lipopolysaccharides molecules remain bound to the bacterial cell. This may account for the ability of anti-lipopolysaccharide MAb 2F11 to react with live *S. enteritidis.*

Since this antibody detects live bacteria virtually exclusively, it can be used for the isolation of *Salmonella enteritidis* from food, clinical and environmental samples heavily contaminated with different microorganisms. This antibody can be also used in conjunction with polymerase chain reaction tests, and as part of an immunosensor for the detection of live *Salmonella enteritidis.*

Finally, the MAb 2F11 can be used for the passive protection of creatures, e.g. chickens, against *Salmonella enteritidis* infections. This can be achieved by an oral administration of MAb 2F11 antibodies. Antibodies can be dissolved in water and delivered to poultry flocks continuously through drinking water over a suitable period of time.

VI. PRODUCTION OF MAb 2F11

The murine monoclonal antibody MAb 2F11 ($IgG_{2\alpha}$) against *Salmonella enteritidis* of the invention can be produced by a fusion of P3X63-Ag8.653 myeloma cells (available from the American Type Culture Collection (Rockville, Md., USA) under accession number ATCC CRL 1580) with spleenocytes of a mouse immunized with heat-attenuated (80° C., 20 min) *S. enteritidis* cells. As already noted, ELISA and SDS-PAGE tests followed by immunoblotting show that MAb 2F11 is specific to $D_1$-serogroup Salmonella exhibiting the highest reactivity with all tested phage types of *S. enteritidis* (1, 4, 8, 13, 13a).

In the original production of the MAb, a group of mice was immunized with heat-attenuated (80° C. for 20 minutes) *S. enteritidis* PT 4 whole cells. The mice responded well, yielding after five injections a dramatic increase in the titre up to 1/100,000. Consequently, mice from this group were sacrificed and three fusions were performed yielding over 500 hybridomas. Of this number, 20 hybridoma lines were found to secrete antibodies which reacted with either cells and/or lipopolysaccharide extracts of *S. enteritidis*. Positive hybridomas were cloned at least twice by limiting dilution and, after each cloning, they were screened against a panel of Salmonella and non-salmonellae spp. Most of the tested hybridomas secreted antibodies which were relatively non-specific, reacting with salmonellae and non-salmonellae spp.

In contrast, a clone 2F11 secreted antibodies that were highly reactive with *S. enteritidis* and showed no reactivity towards other Salmonella serogroups. This clone was propagated as ascitic fluid and the resulting antibodies (MAb 2F11) were purified and used for further studies. As noted above, the MAb 2F11 was of the IgG2a, type immunoglobulin with a lambda light chain as analyzed by a mouse-type subisotyping assay.

Viable samples of the 2F11 clone cells (identified as hybridoma, MAb 2F11) were deposited on May 19, 1995 under the terms of the Budapest Treaty with the American Type Culture Collection of 12301 Parklawn Drive, Rockville, Md. 20852, U.S.A. (Tel: 301-231-5520), under the accession number ATCC HB-11891.

The information provided above is based on a body of detailed experimental work carried out by the inventor of the present invention. This experimental work is discussed and described in the following. However, the information provided below should not be taken as limiting the scope of the present invention.

EXPERIMENTAL PROCEDURE AND DISCUSSION

The antigenic specificity of the MAb 2F11 was analyzed by ELISA using poly-L-lysine pre-coated microplates and lipopolysaccharides as coating antigens extracted from various *S. enteritidis* phage types as well as other $D_1$ serovars (O:1, 9, 12); b/ *S. typhimurium* of serogroup B (O:1, 4, 5, 12), which share the same trisaccharide backbone c/ *S. maarseen* of serogroup $D_2$ (O:9, 46), which share the same tetrasaccharide repeating unit. The antibody was highly reactive to all tested *S. enteritidis* strains exhibiting equal avidity regardless of phage type, as shown in Table 3 below.

TABLE 3

Binding of MAb 2F11 to lipopolysaccharides isolated from different bacteria as assessed by ELISA[a]

| LPS Extract | Absorbance (405 am) |
|---|---|
| S. enteritidis PT 1 | 1.786 |
| S. enteritidis PT 4 | 1.992 |
| S. enteritidis PT 8 | 1.840 |
| S. enteritidis PT 13 | 1.891 |
| S. enteritidis PT 13a | 1.966 |
| S. enteritidis[b] | 1.803 |
| S. gallinarum | 1.423 |
| S. berta | 0.844 |
| S. pullorum | 0.235 |
| S. maarseen | 0.133 |
| S. typhimurium[b] | 0.086 |
| E. coli[b] | 0.056 |

[a]Using microplates pre-coated with poly-L-lysine.
[b]Commercial LPS from Sigma Co.

These properties makes MAb 2F11 a suitable probe for the detection of various phage types of S. enteritidis with equal sensitivity. Furthermore, the antibody was neither reactive with lipopolysaccharide of B-serogroup nor lipopolysaccharides isolated from serovar $D_2$.

This indicated that MAb 2F11 is highly specific for factor 9 (Lipopolysaccharide O-9) present in $D_1$ salmonellae. Similar specificity was reported for a monoclonal antibody produced against S. typhi (Lu et al., 1991). Factor 9 is a part of the D-Salmonella O-antigen and is composed of two monosaccharides; tyvelose and mannose linked through $\alpha 1,3$. The tyvelose residue is a side sugar attached to the trisaccharide repeating unit backbone comprising of mannose, rhamnose and galactose (see FIG. 2). The chemical structure of O-antigen is responsible for the serogroup specificity of salmonellae (Lindberg and Le Minor, 1984). Thus substitution of tyvelose by abequose yields factor 4 which is unique for B salmonellae (FIG. 2). Although the trisaccharide backbone remains the same, lipopolysaccharide O-4 was not recognized by MAb 2F11. This suggested that tyvelose is an essential part of the epitope recognized by this antibody. It appeared also that the nature of the glycosidic bonds between monosaccharides in the trisaccharide backbone play a significant role in the specificity of the antibody. In $D_2$ salmonellae which contains factor 9, mannose is bound to rhamnose via $\beta 1,4$ instead of $\alpha 1,4$ ($D_1$) while the trisaccharide backbone is linked through $\alpha 1,6$ instead of $\alpha 1,2$ ($D_1$) (FIG. 2). Because of this difference, MAb 2F11 shows the lack of reactivity with lipopolysaccharides O-9 of $D_2$ salmonellae (Table 3).

Figure 5:
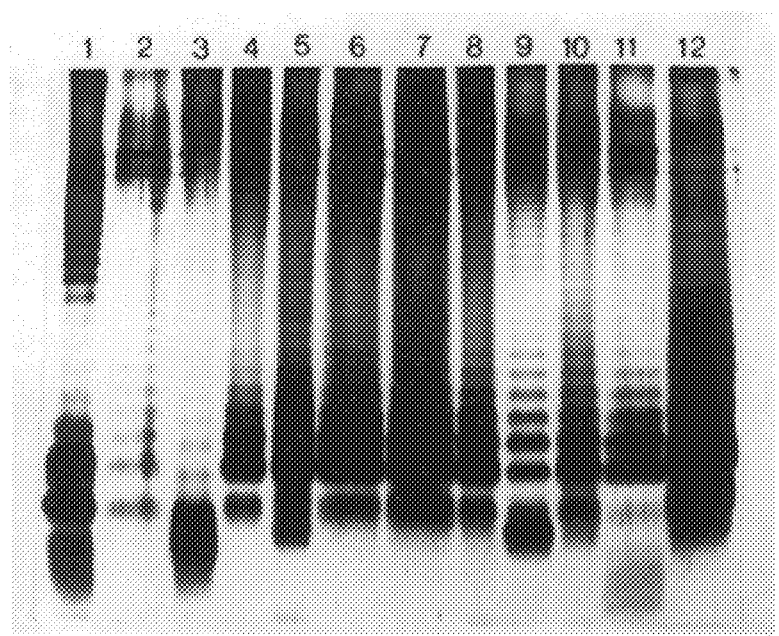

To further investigate the epitope specificity of the MAb 2F11, the lipopolysaccharides from various phage types of Salmonella enteritidis and other $D_1$ serovars as well as from serogroups B, $D_2$ and E. coli were studied by electrophoresis and immunoblotting. Silver staining after SDS-PAGE electrophoresis revealed the heterogeneity of the tested lipopolysaccharides (FIG. 5). All lipopolysaccharide samples yielded ladder-like migration patterns typical for lipopolysaccharides from Gram-negative smooth bacteria. A similar banding pattern has been reported by others (Palva and Makela, 1980) and represents lipopolysaccharide molecules containing increasing numbers of O-antigen repeating units. The highest mobility molecules (closer to bottom of the electrophoregram) is believed to correspond to lipopolysaccharides containing a complete core oligosaccharide but lacking O-antigen units, while slow-migrating molecules (at the higher molecular weight region) represent lipopolysaccharides molecules containing long chain O-antigen (Parent et al., 1992).

Figure 6:
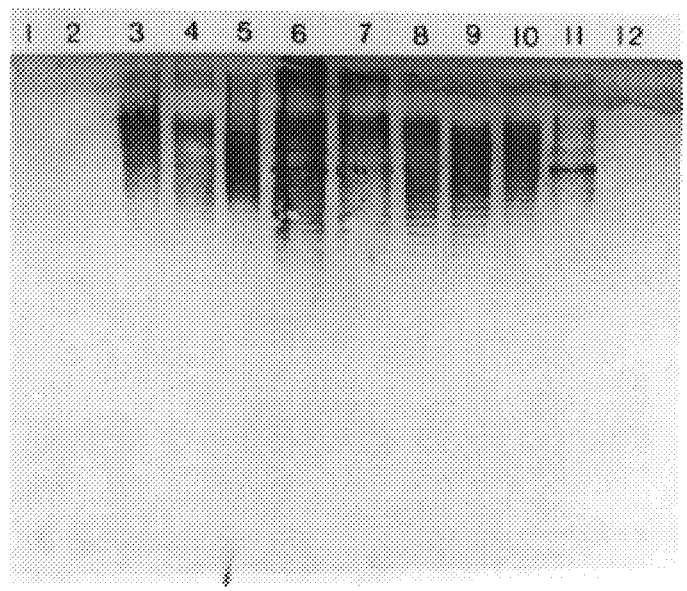

The specificity of MAb 2F11 for lipopolysaccharides O-antigen was confirmed by immunoblotting (FIG. 6). The antibody reacted selectively with lipopolysaccharides isolated from all tested phage types of S. enteritidis (FIG. 6, lanes 3–8) and other $D_1$-serovars (FIG. 6, lanes 9–11) but it did not bind to lipopolysaccharides from serovars B (FIG. 6, lane 2), $D_2$ (FIG. 6 lane 12) and E. coli (FIG. 6, lane 1). The MAb preferentially reacted with a high-molecular weight population of lipopolysaccharides indicating that the sites recognized were in the long chain O-antigen region bearing a specific epitope.

Immunoblotting in concert with ELISA results demonstrated that this epitope, at least in part, was composed of tyvelose and the $\alpha$-mannose residue in the backbone region, since it was shared by all S. enteritidis strains but not S. typhimurium, and S. maarseen.

EXPERIMENTAL DETAIL

Materials

Nutrient broth (NB; Difco Laboratories, Detroit, Mich., USA), standard plate count agar (SPC; Difco), tetrathionate broth (Difco), selenite cysteine broth (Difco) and M-broth (Difco) were obtained from BDH Inc. (Toronto, ON, Canada).

Brain heart infusion broth (BHI) and RPMI-1640 medium were from Gibco (Grand Island, N.Y., USA). Lipopolysaccharides from Escherichia coli, S. typhimurium and S. enteritidis, bovine pancreas ribonuclease and deoxyribonuclease, hypoxanthine, aminopterin and thymidine, Poly-L-lysine (PLL) and p-nitrophenyl phosphate (pnpp) were purchased from Sigma Chemical Co. (St Louis, Mo., USA).

Pristane (2,6,10,14-tetramethylpentadecane) were from Aldrich Chemical Co. (Milwaukee, Wis., USA). Myeloma cells P3X63-Ag8.653 (ATCC CRL 1580) were obtained from American Type Culture Collection (Rockville, Md., USA) while polyethylene glycol 4000 (cat. no. 9727) was from Merck, (Germany). Fetal calf serum was a product of Bocknek Ltd, (Toronto, ON, Canada).

Nitrocellulose membrane (0.45 $\mu$m), diethanolamine buffer, alkaline phosphate-conjugated goat anti-mouse immunoglobulins, mouse-type subisotyping kit, 5-bromo-4-chloro-3-indolyphosphate (BCIP), nitroblue tetrazolium chloride (NBT) were purchased from BioRad, (Hercules, Calif., USA). Microtest III polyvinyl flexible tissue culture plates (Falcon 3912) were obtained from Canlab, (Mississauga, ON, Canada).

All other chemicals and reagents were of analytical grade.

Bacteria and Culture Conditions

Table 2 lists bacteria used for the assessment of the present invention and their sources. All Salmonella strains were prepared by the following procedure. A loopful of stock bacterial culture which was maintained in SPC slants was inoculated into 5 ml of NB and incubated at 37° C. for 16 hours. One ml of turbid NB was placed in 10 ml of tetrathionate broth or selenite cysteine broth and incubated for 24 hours at 42° C. One ml of each of the selective broths were added to 200 ml of M broth and incubated with agitation at 37° C. for 16 hours. The cells were collected by centrifugation, washed twice with saline (0.85% NaCl) and resuspended in saline. Non-salmonellae bacteria were grown in BHI for 16 hours at 37° C., harvested by centrifugation, washed and resuspended in saline. The cell suspensions were diluted to the required concentration, heated for 20 minutes at 80° C. and then used for ELISA as described below. The live bacteria were obtained by washing slant cultures with saline.

Lipopolysaccharide Preparation

Bacterial lipopolysaccharide (LPS) extracts were prepared using the modified method of Johnson & Perry (Can. J. Microbiol., 22, 29–34, 1976). One gram of freeze dried Salmonella cells was resuspended in 20 ml of buffer L and sonicated three times for 30 seconds at 300 W at 4° C. using a BRAUN-SONIC 1510 (trademark) device (B. Braun, Melsungen AG). The suspension was diluted to 100 ml with 20 mM $MgCl_2$ containing 0.1 µg/ml of bovine pancreas ribonuclease and deoxyribonuclease and then incubated for 10 minutes at 37° C., and additional 10 minutes at 60° C. Then, the suspension was mixed with an equal volume of preheated 90% phenol and incubated for 15 minutes at 70° C. The final suspension was centrifuged at 1500× g for one hour. After that, the aqueous phase was collected and dialysed for one week at 4° C. against distilled water which was changed daily. Then lipopolysaccharide extracts were lyophilized and stored at −20° C. until used.

Production of Monoclonal Antibodies

Immunization

Female BALB/c mice (6–8 weeks old) were immunized five times intraperitoneally with $5 \times 10^7$ heat attenuated (80° C. for 20 minutes) cells of S. enteritidis PT 4 at two week intervals. Tailbleedings were performed before the first immunization, a week after each subsequent injection and shortly before the mice were sacrificed. Diluted sera from the tailbleedings were tested for the presence of antibodies against S. enteritidis by an indirect ELISA. The mouse with the highest titre was given a final booster injection, sacrificed 5 days later, the spleen was removed and used for a fusion.

Hybridoma Production

The fusion was performed according to the modified method of Goding ("Monoclonal Antibodies: Principles and Applications", Academic Press, London, 1983). Spleenocytes were fused with P3X63-Ag8.653 myeloma cells at a ratio of 4:1 in RPMI-1640 in the presence of 40% polyethylene glycol 4000. The fused cells were then resuspended in HAT medium (RPMI-1640 with 10% FCS supplemented with $10^{-4}M$ hypoxanthine, $4 \times 10^{-7}M$ aminopterin and $1.6 \times 10^{-5}M$ thymidine) to a concentration of $10^6$ cells $ml^{-1}$, and plated out onto six 96-well tissue culture plates containing $10^4$ peritoneal macrophage feeder cells per well. After two weeks, hybridomas were screened for antibody production against S. enteritidis. Positive hybridomas were cloned at least twice by limiting dilution into 96-well tissue culture microplates containing standard tissue culture medium supplemented with $5 \times 10^4$ feeder cells per well. Growing hybridomas were screened against S. enteritidis, S. typhimurium and E. coli whole cells and LPS using an indirect ELISA.

MAb Propagation and Isotyping

The established Mab 2F11 was propagated in vivo as ascitic fluid according to the procedure of Harlow and Lane ("Antibodies, A Laboratory Manual", Cold Spring Harbor Laboratories, Cold Spring Harbor, N.Y., 1988; the disclosure of which is incorporated herein by reference). Male BALB/c mice (12 to 16 weeks old) were primed with 500 µl of pristane (2,6,10,14-tetramethyldecanoic acid) into the peritoneum. After a week, the mice were injected intraperitoneally with approximately $10^6$ Mab 2F11 hybridoma cells in 0.5 ml of PBS per mouse. When the mouse was noticeably large (one to three weeks), the ascitic fluid was collected by tapping the abdomen of the mouse using a 18 g needle attached to a five ml syringe. A second batch of the ascitic fluid was collected after one to three weeks. All mice were kept no longer than six weeks after injection. They were euthanized with a $CO_2$ overdose. Ascitic fluid was pooled, clarified by centrifugation, and purified by precipitation with 50% saturated ammonium sulphate. Purified ascites was aliquoted and stored at −20° C. until used.

Monoclonal antibodies were isotyped using a mouse isotyping kit following the manufacturer instructions. Immunoglobulin classes, subclasses and light chain specificity were performed on MAbs from ascitic fluid.

ELISA Protocol

Screening antisera, spent media and ascites for the presence of antibodies towards S. enteritidis was performed by an indirect non-competitive ELISA using polyvinyl chloride Microtest III plates which were coated with either bacterial cell suspensions or lipopolysaccharide extracts.

Bacteria whole cells (100 µl, $10^7$ cells/well) in carbonate buffer (pH 9.6) were added to the plates and incubated overnight at 4° C. After the plates were washed five times with PBST (PBS with 0.5% TWEEN 20), they were blocked by incubating for 2 hours at room temperature with 200 µl/well of PBST containing 5% (w/v) skim milk. After washing four times with PBST, 100 µl of monoclonal antibody (hybridoma spent media, ascites fluid or appropriate dilution of antiserum) in PBST containing 0.1% (w/v) skim milk was added to plates followed by 1 hour incubation at 37° C. Hybridoma spent medium was diluted 1:1, while ascitic fluid was diluted 1:1,000 prior to use. The plates were washed four times with PBST, and 100 µl/well of goat anti-mouse IgG alkaline phosphatase conjugate (diluted 1:3000 in PBST containing 0.1% skim milk) was added, followed by incubation for 1 hour at 37° C. The plates were again washed four times with PBST and then developed by adding 100 µl/well (1 mg/ml) of ρ-nitrophenol phosphate in 0.1M diethanolamine buffer, pH 9.8, and incubated overnight at room temperature. The plates were read at λ 405 nm using a TITERTEK MULTISKAN (trademark) ELISA plate reader (Flow Laboratories, McLean, Va.). Pre-immune sera were used as a negative control.

When lipopolysaccharides was used as an antigen, microplates were pre-coated with poly-L-lysine. Briefly, 100 µl/well of poly-L-lysine (20 µg/ml) in PBS (pH 7.2) was used to coat 96-well plates for 30 min at 37° C. After washing three times with distilled water, plates were coated with 100 µl/well of lipopolysaccharide (10 µg/ml) in distilled water overnight at 4° C. The plates were developed as described above.

Electrophoresis and Immunoblotting

SDS-PAGE

Sodium dodecyl sulphate polyacrylamide gel electrophoresis (SDS-PAGE) was performed according to the method of Laemmli (Nature, 227, 680–685, 1970) in a PROTEAN II (Trademark) cell vertical electrophoresis apparatus (BioRad, Hercules, Calif., USA). Separating and stacking gels contained 15%, and 4% acrylamide, respectively. Lipopolysaccharide extracts were dissolved in sample buffer containing β-mercaptoethanol, heated for 5 minutes at 100° C. and loaded on the gel at a concentration of 10 µg (20 µl) per well. The gels were run at a constant current (30 mA per slab gel) and after electrophoresis was completed, the gels were either developed or submitted to electroblotting. The development of gels were performed using a silver staining procedure according to Kittelberg & Hilbink (J. Biochem. & Biophys. Methods, 26, 81–86, 1993).

Immunoblotting

Immediately after electrophoresis, separated lipopolysaccharides were electrophoretically transferred from the SDS-PAGE gel onto 0.45 µm nitrocellulose membrane using a TRANS-BLOT (trademark) cell (BioRad, Richmond, Calif., USA). The electroblotting was carried out for 16 hours at a constant current (180 mA) at 4° C. (Weintraub et al., J. Bateriol., 174, 1916–1922, 1992). The NC membrane was blocked by incubating in 5% skim milk in TBS (20 mM Tris, 500 mM NaCL, pH 7.5) for 2 hours with shaking at room temperature. Then, the membrane was washed four times with TBST (TBS with 0.05% TWEEN 20) and incubated with MAb diluted 1:25 in BLOTTO (trademark) (TBST containing 1% skim milk) overnight at 4° C. Next, the NC membrane was washed four times with TBST and incubated with goat anti-mouse IgG alkaline phosphatase conjugate (diluted 1:3000 in BLOTTO) for 1 hour at room temperature. The membrane was washed four times with TBST and then developed by incubating in BCIP/NBT substrate solution for 30 minutes at room temperature. Colour development was stopped by rinsing the membrane with warm distilled water.

The invention is further illustrated by the following Examples, provided for illustrative purposes only.

EXAMPLE 1

Pre-enrichment of Salmonella

Large grade A eggs were scrubbed with 70 ethanol, aseptically opened and the contents placed in stomacher bags. The eggs were mixed for 20 seconds in a stomacher and 25 g portions were aliquoted into 50 ml plastic centrifuge tubes. To each tube, one ml of live *S. enteritidis* PT 4 was added to a final concentration of either a one, five, 50 or 500 cell/ml. To the negative control, three ml of saline was added. The eggs mixtures were incubated at 37° C. for 20 hours.

Culture Method

Following incubation, one ml of egg mixture was sampled from each tube to determine viable counts. Egg samples were serially diluted, plated on Standard Count Plate Agar (SPC, Difco Laboratories, Detroit, Mich.) and incubated at 37° C. for 48 hours. Counting colonies were performed on all agar plates using a colony counter.

In addition, one ml of egg mixture from each sample (inoculated and control) was added to 9 ml of Selenite Cysteine Broth (SC, Difco) and incubated at 37° C. overnight. Recovery of Salmonella was confirmed by streaking SC broth onto Brilliant Green Agar (Difco) followed by incubation at 37° C. for additional 24 hours.

Sample Preparation

The egg samples were mixed with 2.5 ml of 15% sodium cholate solution in PBS and heated at 100° C. for 10 minutes to allow the eggs to solidify. The samples were then cooled at 4° C. for 20 minutes. With the aid of a sterile core borer (10 cm in diameter), egg core samples were taken and cut into discs of two mm thick using a sterile surgical blade.

Dot-blot Assay

Egg discs were placed on a pre-wet 0.45 µm nitrocellulose membrane strip (8.5×2.5 cm) and incubated for five minutes at room temperature. The discs were removed and the strip was washed twice with PBS (pH 7.2) for two minutes, and blocked by incubating for one hour at room temperature with Tris-buffered saline (TBS, 25 mM Tris, pH 8.0) containing 5% skim milk. After washing twice for five minutes with TTBS (TBS containing 0.5% TWEEN 20), the strip was incubated with MAb 2F11 for one hour at 37° C. The strip was washed again twice with TTBS and incubated for one hour at room temperature with biotinylated goat anti-mouse IgG (B-GAM) diluted 1:3,000 in TTBS containing 0.1% skim milk. After washing twice with TTBS, the strip was further incubated for one hour at room temperature with a streptavidin alkaline phosphatase conjugate diluted 1:3,000 in TTBS containing 0.1% skim milk. The strip was washed again twice with TTBS and developed by incubating for about 30 minutes at room temperature with BCIP/NBT substrate solution. To stop colour formation, the strip was washed twice in distilled water.

Table 4 and FIG. 1 show the detection limit of the pre-enrichment/dot-blot test system for determination of *S. enteritidis* in eggs. A total of 90 egg samples was assessed for the presence of *S. enteritidis*. Artificially inoculated eggs with the different level of bacteria ranging from one to 500 cells/25 g of eggs yielded approximately $10^6$ to $10^9$ CFU/ml after 20 hours incubation at 37° C. All inoculated egg samples (72) were tested positive by both dot-blot assay and culture method. Uninoculated egg samples (18) yielded negative results (Table 4 and FIG. 1). The obtained results showed that the dot-blot assay was equally effective as the culture method, yet it can be performed faster and with less labour.

TABLE 4

Recovery of *S. enteritidis* from artificially inoculated eggs by dot-blot and culture methods.

| Initial Inoculum (cells/25 g of egg) | Counts after incubation for 20 h at 37° C.[a] | Positive by egg-blot[b] | Positive by culture method |
|---|---|---|---|
| 500 | $2.1 \times 10^9$ (1.0–3.4) | +++ | Yes |
| 50 | $3.3 \times 10^8$ (1.7–4.8) | +++ | Yes |
| 5 | $1.9 \times 10^7$ (1.1–3.7) | ++ | Yes |
| 1 | $2.8 \times 10^6$ (0.8–5.2) | + | Yes |
| 0 | $<10^1$ | – | No |

[a]Mean and range ( ) of 18 samples.
[b]Blot assay was determined for the mean of the viable count at each inoculum level. Egg-blot reaction rating was determined by how quickly the colour development was evident after substrate addition. A rating of +++ colour development was noted within 5 minutes; ++ indicates a colour development within 10 minutes; + indicates colour development within 20 minutes; – No colour development within 40 minutes of substrate addition.

ADDITIONAL EXAMPLES

The following enzyme-linked immunosorbent assays (ELISA) may be used for the detection of *S. enteritidis* in a variety of food and environmental samples. All of the assays detect *S. enteritidis* from enrichment cultures. Prior to determination of this pathogen by ELISA, all samples have to be subjected to enrichment procedure as exemplified below.

Enrichment of Salmonella

Enrichment of *S. enteritidis* may be performed according to the approved methods of the Bacteriological Analytical Manual (US FDA. 1984. Chap. VII In "Bacteriological Analytical Manual," 6th ed. p. 1, Food and Drug Admin., Washington, D.C.) and the AOAC (AOAC. 1995. Chap. 17, Subchap. 9 In "Official Methods of Analysis," p.55, Assn. Off. Anal. Chem., Arlington, Va.). Enrichment usually comprises a three-step procedure: pre-enrichment, selective enrichment and post-enrichment. Briefly, about 25 g of sample contaminated with *Salmonella enteritidis* is added to 225 ml of Lactose Broth (LB, Difco) and incubated for six to 18 hours at 37° C. One ml of LB broth is inoculated into 9 ml of SC broth and incubated at 37° C. for six to 18 hours at 37° C. Then, one ml of SC broth is transferred into 9 ml of M broth (Difco) and incubating again for six to 18 hours at 37° C. After all incubation steps, one ml of M Broth is mixed with detergent (e.g., 15% sodium cholate) and boiled for 10 minutes, cooled to room temperature and used for ELISA. The inventor of the present invention has found that the presence of sodium cholate does not interfere with ELISA involving MAb 2F11.

EXAMPLE 2

Use of MAb 2F11 in an Indirect Noncompetitive ELISA

ELISA microplates were pre-coated with poly-L-lysine. Briefly, 100 $\mu$l/well of poly-L-lysine (20 $\mu$g/ml) in PBS (pH 7.2) was used to coat 96 well plates for 30 minutes at 37° C. After washing three times with distilled water, plates were incubated with 100 $\mu$l/well of enriched sample (M Broth) overnight at 4° C. or for one hour at 37° C. After the plates were washed five times with PBST (PBS with 0.5% TWEEN 20), they were blocked by incubating for two hours at room temperature with 200 $\mu$l/well of PBST containing 5% (w/v) skim milk. After washing four times with PBST, 100 $\mu$l of MAb 2F11 in PBST containing 0.1% (w/v) skim milk was added to plates followed by one hour incubation at 37° C. The plates were washed four times with PBST, and 100 $\mu$l/well of a goat anti-mouse IgG alkaline phosphatase conjugate (diluted 1:3,000 in PBST containing 0.1 skim milk) was added, followed by incubation for one hour at 37° C. The plates were again washed four times with PBST and then developed by adding 100 $\mu$l/well (1 mg/ml) of p-nitrophenol phosphate in 0.1M diethanolamine buffer, pH 9.8, and incubated overnight at room temperature. The plates were read at $\lambda$ 405 nm using a TITERTEK MULTISKAN (trademark) ELISA plate reader (Flow Laboratories, McLean, Va.).

EXAMPLE 3

Analysis of Non-egg Food Samples Using Egg Matrix

Nine chicken meat samples (25 g each) contaminated with *Salmonella enteritidis* (10 to $10^8$ cells/25 g) were blended for two minutes with lactose broth (225 ml) in a stomacher and incubated at 37° C. for six hours. Subsequently, 1 ml of broth was transferred to 25 g of homogenized liquid egg free of bacteria. The contents were mixed for 30 seconds in a stomacher and the mixtures were incubated at 37° C. for an additional 18 hours. After incubation, the mixture was mixed with a detergent, solidified upon temperature treatment and used for the dot-blot assay as described in Example 2. All contaminated chicken meat samples tested positive for Salmonella.

EXAMPLE 4

Use of MAb 2F11 in a Direct Noncompetitive ELISA

Direct ELISA is performed essentially as indirect ELISA with some modifications. MAb 2F11 conjugated with alkaline phosphatase (or other suitable enzyme) is used. Consequently, the addition of goat anti-mouse IgG alkaline phosphatase, followed by the incubation step is eliminated.

EXAMPLE 5

Use of MAb 2F11 in a Sandwich ELISA

Since an epitope recognized by MAb 2F11 is abundant within a LPS molecule as well as on a *S. enteritidis* cell (FIG. 3A, 3B), the MAb 2F11 can be used in the sandwich ELISA format as a capture and detector antibody. In this respect, ELISA microplates are coated with MAb 2F11. Briefly, 100 $\mu$l/well of antibody solution (10 $\mu$g protein/ml) in PBS (pH 7.2) is used to coat 96-well plates for overnight at 4° C. Next, the plates are blocked by incubating for one hour at room temperature with 200 $\mu$l/well of PBST containing 5% (w/v) skim milk. After washing three times with distilled water, plates are incubated with 100 $\mu$l/well of enriched sample (M Broth) in PBS overnight at 4° C. or for one hour at 37° C. After the plates are washed five times with PBST (PBS with 0.5% TWEEN 20), they are blocked by incubating for one hour at room temperature with 200 $\mu$l/well of PBST containing 5% (w/v) skim milk. After washing four times with PBST, 100 $\mu$l of a biotinylated MAb 2F11 in PBST containing 0.1% (w/v) skim milk is added to plates followed by one hour incubation at 37° C. The plates are washed four times with PBST, and 100 $\mu$l/well of streptavidin is added, followed by incubation for one hour at 37° C. Next, 100 $\mu$l/well biotinyleted alkaline phosphatase in PBST containing 0.1% skim milk is added, followed by incubation for one hour at 37° C. The plates are again washed four times with PBST and then developed by adding 100 $\mu$l/well (1 mg/ml) of p-nitrophenol phosphate in 0.1M diethanolamine buffer, pH 9.8, and incubated overnight at room temperature. The plates are read at $\lambda$ 405 nm using a TITERTEK MULTISKAN ELISA plate reader (Flow Laboratories, McLean, Va.).

EXAMPLE 6

Use of MAb 2F11 in an Immunocapture Probe

In addition, MAb 2F11 can be immobilized on a solid support and used as an immunocapture probe to isolate live bacteria from food, clinical and environmental samples. There are different solid supports such as polystyrene and polyvinyl chloride tubes, dipsticks or beads, magnetic and supermagnetic (e.g., DYNABEADS M-280) beads used for that purpose. The capture probe is prepared by coating a solid support with antibody solution (10 $\mu$g protein/ml) in PBS (pH 7.2) overnight at 4° C. After washing, the coated support is blocked by incubating for one hour at room temperature with PBST containing 5% (w/v) skim milk. Before use, the support is washed three times with PBST containing 0.1% (w/v) skim milk.

Isolation of bacterial cells from samples using the immunocapture probe employs two step procedure: pre-enrichment and selective concentration of live bacterial cells prior secondary enrichment. Briefly, 25 g of sample contaminated with *Salmonella enteritidis* is added to 225 ml of lactose broth, universal enrichment broth, buffer peptone water or other suitable medium, and incubated for six to 18 hours at 37° C. Subsequently, pre-enrichment broth is contacted with the antibody-coated support for 30 to 60 minutes at 37° C. to allow for selective attachment of Salmonella cells. After incubation, the support is separated from broth, washed three times with PBST containing 0.1% (w/v) skim milk and contacted with enrichment broth such as M-broth for six hours at 37° C. The letter step is necessary to propagate Salmonella to the level needed for detection by the dot-blot method. Following incubation, enrichment broth is mixed with detergent (e. g., 15% sodium cholate) and the mixture is heated at 100° C. for 10 min, cooled to room temperature and spotted on a pre-wet nitrocellulose membrane. The dot-blot assay is performed as described above. Alternatively, enriched samples can be analyzed for Salmonella by any ELISA described earlier or by a nucleic acid hybridization assay.

What I claim is:

1. A method of testing for the presence of a pathogenic microorganism in an egg, comprising:

aseptically homogenizing a sample of the egg to form a uniform moisture-containing egg matrix;

incubating the egg matrix for a period of time and at a temperature to cause propagation of the microorganism present in the matrix;

adding a detergent to the incubated matrix to separate antigen molecules from surfaces of cells of the microorganism and to distribute the antigen molecules throughout the egg matrix;

heating said egg matrix to cause gellation of said matrix;

contacting the gelled egg matrix with an absorbent inert support to cause transfer of the antigen molecules present in said gelled egg matrix to said support;

contacting said support with a detector antibody for said antigen molecules to form antigen-antibody complexes with antigen molecules present on said support; and detecting antigen-antibody complexes present on said support, wherein the detection of said antigen-antibody complexes indicates the presence of said pathogenic microorganism.

2. A method according to claim 1 wherein said pathogenic microorganism is a bacterium.

3. A method according to claim 1 wherein said pathogenic microorganism is a $D_1$-serovar of Salmonella.

4. A method according to claim 1 wherein said pathogenic microorganism is selected from the group consisting of *Salmonella enteritidis, Salmonella berta, Salmonella gallinarum* and *Salmonella pulorum*.

5. A method according to claim 1 wherein said pathogenic microorganism is a phage type of *Salmonella enteritidis*.

6. A method according to claim 1 wherein said egg matrix is heated immediately after said adding of said detergent.

7. A method according to claim 1 wherein said detergent is a member selected from the group consisting of sodium cholate, cholic acid and deoxycholate.

8. A method according to claim 1 wherein said antibody is a biotinylated monoclonal antibody and said antigen-antibody complexes are detected by incubating said complexes with avidin/streptavidin-alkaline phosphatase conjugate and 5-bromo-4-chloro-3-indylphosphate ρ-toluidine salt/nitroblue tetrazolium chloride substrate solution.

9. A method according to claim 3 wherein said antibody is a $D_1$-serospecific murine hybridoma monoclonal antibody directed against a *Salmonella enteritidis* lipopolysaccharide O-9.

10. A method according to claim 9 wherein said antibody is MAb 2F11 (American Type Culture Collection Accession Number ATCC HB-11891).

11. A method of testing for the presence of a pathogenic microorganism in a foodstuff or other material, wherein said foodstuff is other than egg, comprising:

aseptically blending pre-enriched sample of the foodstuff or other material with liquid egg to form a matrix;

incubating the matrix for a period of time and at a temperature to cause propagation of the microorganism present in the matrix;

adding a detergent to the incubated matrix to separate antigen molecules from surfaces of cells of the microorganism and to distribute the antigen molecules throughout the egg matrix;

heating said incubated matrix to cause gellation of said incubated matrix;

contacting the gelled matrix with an absorbent inert support to cause transfer of the antigen molecules present in said gelled matrix to said support;

contacting said support with a detector antibody for said antigen molecules to form antigen-antibody complexes with antigen molecules present on said support; and detecting antigen-antibody complexes present on said support, wherein the detection of said antigen-antibody complexes indicates the presence of said pathogenic microorganism.

12. A method of testing for the presence of *Salmonella enteritidis*, or other $D_1$ serovar of Salmonella, in contents of an egg, comprising:

aseptically accessing said contents within said egg;

incubating the contents for a period of time and at a temperature to cause propagation of any *Salmonella enteritidis* or said other $D_1$ Salmonella serovar, present in the contents;

adding a detergent to the incubated contents to release antigen from cells of said *Salmonella enteritidis* or said other $D_1$ Salmonella serovar;

heating the contents to a temperature that causes gelling to form gelled egg contents;

contacting said gelled egg contents with an absorbent inert support to cause transfer of said antigen, if present in said gelled egg contents, to said support by diffusion;

contacting said support with an antibody directed against *Salmonella enteritidis* lipopolysaccharide O-9 to form antigen-antibody complexes with any *Salmonella enteritidis* antigen present on said support; and detecting any antigen-antibody complexes on said support, wherein the detection of said antigen-antibody complexes indicates the presence of *Salmonella enteritidis* or other $D_1$ serovar of Salmonella.

13. A method of testing for *Salmonella enteritidis* or other $D_1$ serovars of Salmonella in a sample of a material, comprising:

incubating said sample in a culture medium suitable for growth and propagation of said *Salmonella enteritidis* or other $D_1$ serovar of Salmonella;

contacting said culture medium with MAb 2F11 antibody (American Type Culture Collection Accession Number ATCC HB-11891) bound to an inert support;

separating the support from the culture medium and contacting said support with a further culture medium to further propagate said *Salmonella enteritidis* or $D_1$ serovars of Salmonella;

adding a detergent to said further culture medium; and testing for the presence of an antigen derived from said *Salmonella enteritidis* or other $D_1$ serovars of Salmonella in said further culture medium by an enzymatic-linked immunosorbent assay, wherein the presence of said antigen indicates the presence of *Salmonella enteritidis* or other $D_1$ serovar of Salmonella.

14. A method according to claim 13 wherein said further culture medium, following said adding of a detergent, is heated and then cooled to ambient temperature prior to said testing.

15. A method according to claim 14 wherein the further culture medium is heated to boiling for about ten minutes.

16. A method according to claim 13 wherein said further culture medium is tested by spotting a quantity of the medium onto an absorbent inert support, contacting said support with a detector antibody for said antigen to form antigen-antibody complexes with antigen present on said support; and detecting antigen-antibody complexes present on said support.

17. A method of removing live cells of *Salmonella enteritidis* from a sample, comprising:

contacting said sample with Mab 2F 11 antibody (American Type Culture collection Accession Number ATCC HB-11891) bound to a solid support to form antigen-antibody complexes between said live cells and the bounds Mab 2F11 antibody; and removing said solid support from said sample wherein said live cells remain as antigen antibody complexes bound to said solid support.

* * * * *